(12) United States Patent
Blamey et al.

(10) Patent No.: US 9,084,892 B2
(45) Date of Patent: Jul. 21, 2015

(54) SOUND PROCESSOR FOR A COCHLEAR IMPLANT

(75) Inventors: Peter J. Blamey, South Yarra (AU); Brett A. Swanson, Meadowbrook (AU); Hugh McDermott, Macedon (AU); James F. Patrick, Roseville (AU); Graeme M. Clark, Eltham (AU)

(73) Assignee: Cochlear Limited, Macquarie University, NSW (AU)

( * ) Notice: Subject to any disclaimer, the term of this patent is extended or adjusted under 35 U.S.C. 154(b) by 1266 days.

(21) Appl. No.: 11/453,043

(22) Filed: Jun. 15, 2006

(65) Prior Publication Data

US 2006/0235486 A1 Oct. 19, 2006

Related U.S. Application Data

(63) Continuation of application No. 10/257,796, filed as application No. PCT/AU01/00723 on Jun. 19, 2001, now Pat. No. 7,082,332.

(30) Foreign Application Priority Data

Jun. 19, 2000 (AU) ...................................... PQ 8205

(51) Int. Cl.
*A61N 1/05* (2006.01)
*A61N 1/36* (2006.01)
*H04R 25/00* (2006.01)

(52) U.S. Cl.
CPC .......... *A61N 1/36032* (2013.01); *H04R 25/356* (2013.01); *H04R 25/505* (2013.01); *H04R 2225/43* (2013.01)

(58) Field of Classification Search
CPC .......................... A61N 1/0541; A61N 1/36032

USPC ................................................. 607/55, 56, 57
See application file for complete search history.

(56) References Cited

U.S. PATENT DOCUMENTS

| | | | | |
|---|---|---|---|---|
| 4,532,930 A | * | 8/1985 | Crosby et al. | 607/57 |
| 4,617,913 A | * | 10/1986 | Eddington | 607/57 |
| 5,381,512 A | * | 1/1995 | Holton et al. | 704/200.1 |

(Continued)

FOREIGN PATENT DOCUMENTS

| | | |
|---|---|---|
| EP | 0282335 B1 | 9/1988 |
| EP | 1146774 | 10/2001 |
| WO | 95/01709 | 1/1995 |

OTHER PUBLICATIONS

Canadian Search Report. CA Application No. 2,405,523. Mailed Feb. 11, 2009.

(Continued)

*Primary Examiner* — Catherine Voorhees
*Assistant Examiner* — Michael D Abreu

(57) ABSTRACT

The sound processor and method uses a model of basilar membrane motion to select stimuli, based upon the predicted motion which the acoustic signal presented would produce in an acoustically excited normally hearing cochlea. The filter; used, in contrast to single channel per electrode approaches, cover multiple channels and overlap with each other. Consequently the stimuli presented produce a neural excitation pattern which approximates the spatio-temporal travelling wave observed on the basilar membrane in an acoustically excited normally hearing cochlea. Preferably, the predicted electrode stimuli are based upon the instantaneous predicted amplitude of the electrode location.

34 Claims, 6 Drawing Sheets

(56) References Cited

U.S. PATENT DOCUMENTS

| | | | |
|---|---|---|---|
| 5,388,182 A | 2/1995 | Benedetto et al. | |
| 6,002,966 A | 12/1999 | Loeb et al. | |
| 6,064,913 A | 5/2000 | Irlicht et al. | |
| 6,480,820 B1 * | 11/2002 | Clopton et al. | 704/203 |
| 6,575,894 B2 * | 6/2003 | Leysieffer et al. | 600/25 |

OTHER PUBLICATIONS

International Search Report dated Aug. 17, 2000 for International Patent Appln. No. PCT/AU01/00723.

Written Opinion for International Appln. No. PCT/AU01/00723 dated Jan. 11, 2002.

International Preliminary Examination Report dated Jul. 24, 2002 for International Patent Appln. No. PCT/AU01/00723.

McDermott, H., et al., "A Portable Programmable Digital Sound Processor for Cochlear Implant Research," IEEE Transactions on Rehabilitation Engineering, pp. 94-100, Jun. 1993.

Supplemental European Search Report for EP 01942897 dated May 11, 2005.

* cited by examiner

SOUND PROCESSOR FOR A COCHLEAR IMPLANT

TECHNICAL FIELD

The present invention relates to cochlear implants, and to sound processing devices and methods relating to cochlear implants.

BACKGROUND ART

In normal hearing, sound causes mechanical vibrations that stimulate the hair cells of the cochlea to produce electrical impulses that travel down the auditory nerve where they are perceived by the brain as sound. If for some reason these hair cells are destroyed or not present within the cochlea, as is the case with individuals with severe or profound hearing loss, the nerve cells do not receive this electrical stimulation, therefore no sound is perceived. A cochlear implant attempts to replace this lost function by providing artificial electrical stimulation of the surviving auditory nerve. Cochlear implants have been in clinical use for many years. Such devices use an array of implanted electrodes to provide electrical stimuli to the cochlea. The electrical stimuli are determined by a processor responsive to speech and sound signals in the environment of the user.

Historically, prior to around 1994, the majority of speech processors used in conjunction with a cochlear implant employed speech processing strategies that can be described as Feature Extraction Strategies. In such strategies, the associated implant hardware attempts to identity the speech features present in the detected sound signal and encodes such features as patterns of electrical stimulation. Feature extraction strategies have the advantage that the hardware required to perform the feature extraction is relatively simple and consumes a relatively low amount of power.

With improvements in silicon chip technology and an increased knowledge of the safety of electrical stimulation, a new approach in sound processing became possible. This approach had the ability to provide a full range of spectral information of the speech signal without the need for the hardware to fit the signal into a preconceived mould, giving the patent the opportunity to listen to the particular information of interest, within background noise, providing a more realistic approach to speech processing. Such sound processors use band-pass filters to separate acoustic signals into frequency bands or spectral components with relatively little overlap of the bands, with the electrodes being stimulated in a tonotopic fashion according to the energy in those bands. Usually they present a smoothed (low-pass-filtered) representation of the amplitude from each band to a single electrode.

Despite considerable practical success with each of the existing schemes, the user perceptions of existing devices indicate that there are significant outstanding problems. Three fundamental problems of sound perception reported by cochlear implant users are poor frequency resolution and discrimination, poor perception of speech in noise at low signal-to-noise ratios, and poor perception of musical sounds.

It is an object of the present invention to provide an alternative speech processor and processing method, in order to further improve the practical performance of the cochlear implant system.

SUMMARY OF THE INVENTION

In broad terms, the present invention provides a fundamental change to the traditional approach used in sound processing for cochlear implants. Instead of attempting to separate acoustic information into discrete frequency bands or channels, the inventive processor produces electrical stimulation patterns that excite broad overlapping regions of the cochlea. It is believed that the approach of the present invention will provide a better approximation to the behavior of the auditory structures during hearing by a normally hearing listener. Current processors produce localised stimuli based upon the frequency of components of the sound signal. In contrast, the present invention seeks to approximate the spatio-temporal neural excitation patterns which are induced by the motion of the basilar membrane as a response to sound stimuli in the normally hearing listener. The present invention seeks to produce a spatio-temporal pattern of stimulation along the length of an intra-cochlea electrode array, as opposed to merely localised stimuli.

According to a first aspect, the present invention resides in a method of processing sound signals in order to generate electrical stimuli for an auditory prosthesis whereby a neural excitation pattern is produced which mimics the spatio-temporal pattern associated with the travelling wave observed on the basilar membrane in an acoustically excited normally-hearing cochlea.

According to another aspect, the present invention provides a sound processor for use in a cochlear implant system, said sound processor being of the type which receives sound signals from a microphone or the like, processes said signals according to a predetermined instruction set, and provides stimulation instructions for an Implanted electrode array, characterized in that the predetermined instruction set produces stimulus instructions which are intended to provide an approximation to the spatio-temporal waveforms induced in response to said sound signals on the basilar membrane of a normal hearing listener.

According to yet another aspect, the present invention provides a method of processing sound signals so as to produce stimulus instructions for a cochlear implant, including the steps of deriving the vector of complex Fourier transform coefficients for a data sample;

multiplying the vector of the coefficients by a complex matrix representing the amplitude and phase of the Fourier frequency components at the position of the electrodes in the cochlea relative to the amplitude and phase at the stapes in a normal ode to produce an output vector; and converting the output vector values to electrode current levels.

Travelling wave aspects of basilar membrane response have been observed and reported on in investigations of normal auditory processes. However, them has been no previous attempt to utilise these phenomena as an element of stimulus processing for cochlear implants. The travelling wave may be thought of as a 3-Dimensional pattern in which the dimensions are time, distance along the basilar membrane, and displacement of the basilar membrane. The properties of these patterns that are thought to be important (and different from existing processor outputs) include a diagonal ridge structure of the 3D pattern, the dynamic nature of the ridge pattern that sweeps across the cochlear electrode array at a particular velocity that depends on position, the smoothly varying nature of the pattern in both space and time, and the maintenance of naturally-occurring phase and amplitude relationships between the stimulation patterns on individual electrodes.

BRIEF DESCRIPTION OF DRAWINGS

The implementation of the present invention will be described in more detail with reference to the accompanying drawings, in which.

DETAILED DESCRIPTION

The present invention will be described with reference to the hardware implementation used by the applicant, using an Implanted receiver/stimulator unit and an external speech processor and microphone. However, the present invention is of broad scope and can be implemented on any sufficiently sophisticated cochlear implant system. In particular, it is anticipated that the present invention will be able to be implemented more fully and in more detail on future generations of cochlear implants, with increased processing power and flexibility relative to the current state of the art. The present invention could also be implemented in a totally implanted device, or some intermediate stage between the present systems and a totally implanted device.

Figure 1:
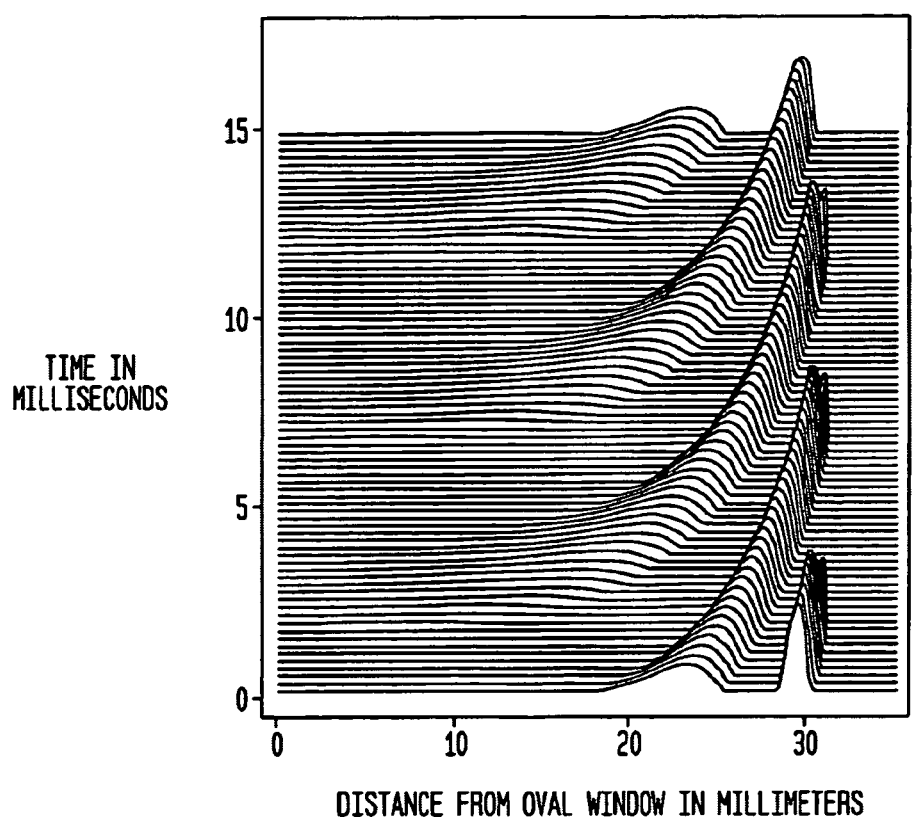
FIG. 1 is a graph illustrating a travelling wave excitation pattern produced in response to a pure tone of frequency 200 Hz.

The essential difference between the invention described and previous implant coding schemes is that the importance of overlapping information across electrodes is recognized and a complex spatio-temporal pattern is produced. This pattern preserves, at least in part, the detailed amplitude and phase relationships between different positions that occur normally in an intact cochlea. These amplitude and phase relationships vary smoothly as a function of position along the cochlea to produce the acoustic "travelling wave" (von Bekesy, 1961). Instead of attempting to separate acoustic information into discrete frequency bands or channels, the travelling wave processor produces electrical stimulation patterns that excite broad overlapping regions of the cochlea. As an example, FIG. 1 shows the excitation pattern that is produced by the inventive travelling wave processor in response to a pure tone input signal. Each line in the Figure shows the shape of the excitation function at an instant in time. The horizontal axis represents position along the cochlea from the basal (high frequency) end on the left to the apical (low frequency) end on the right.

In contrast the excitation pattern produced by the same pure tone input signal after processing by any of the currently used cochlear implant coding schemes would be localized to one position in the cochlea and represented by a narrow ridge running vertically up the page in a Figure analogous to FIG. 1. In some cochlear implant coding schemes the amplitude of the vertical ridge would be represented by electrical pulses at a fixed rate and level (ACE, SPEAK), or modulated at a rate equal to the frequency of the (low-frequency) input tone (F0F2, F0F1F2, MPEAK, CIS, SAS). In the latter cases, the excitation pattern is effectively a vertical slice taken from the pattern of FIG. 1 at the point where the amplitude of the pattern is greatest.

It is hypothesized that the auditory pathways of the brain have specialized perceptual mechanisms designed to recognize characteristics of 3-dimensional (position X time X amplitude) excitation patterns like those shown in FIG. 1. If is known that the visual and tactile sensory systems have neural mechanisms specialized to detect the orientation and spacing of stripes and ridges. The auditory system may be programmed in an analogous manner to recognise the diagonal ridges of patterns like the one in FIG. 1. If an incomplete pattern is presented to the cochlea (as in all prior art cochlear implant coding schemes) these perceptual mechanisms will be engaged but will not operate as effectively as they would if the whole pattern was presented. It is hypothesized that the presentation of complete 3D patterns will improve the perception of sound by cochlear implant users and overcome or reduce some of the problems that are common to all prior art cochlear implant systems. Relative to normal hearing listeners, the problems for implant users include poor frequency discrimination and resolution abilities, poor speech recognition of speech in background noise, and lack of musical quality for processed musical sounds.

Figure 2:
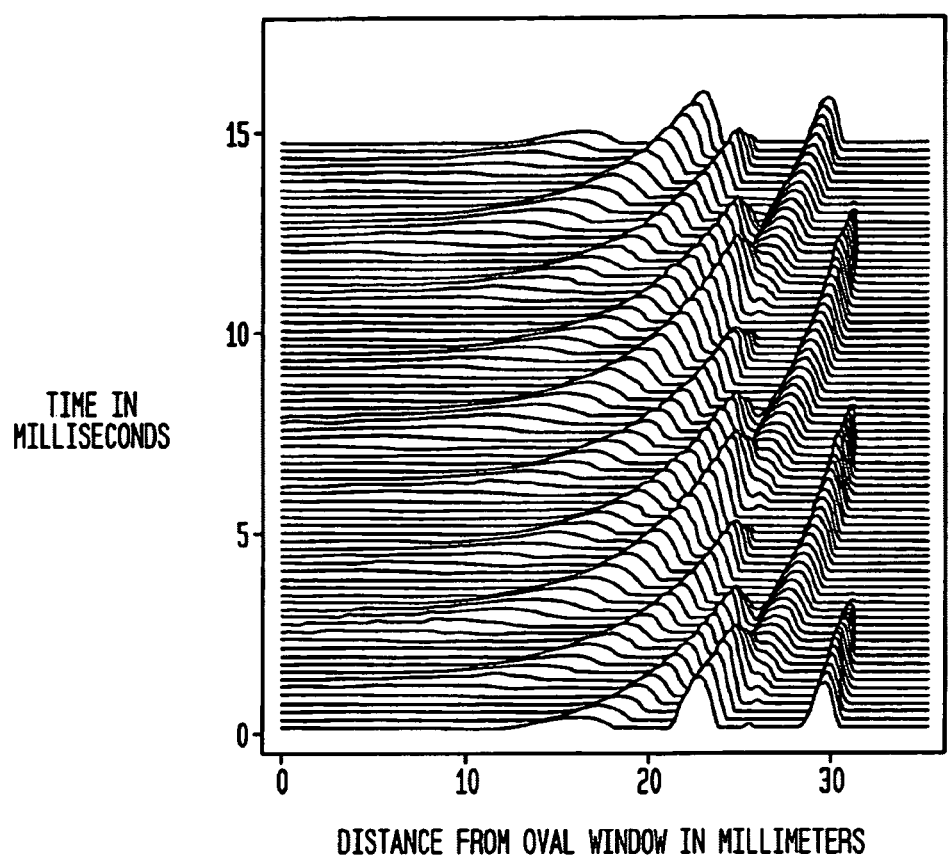
FIG. 2 is a graph illustrating a travelling wave excitation pattern for tones at 200 and 600 Hz.
Figure 3:
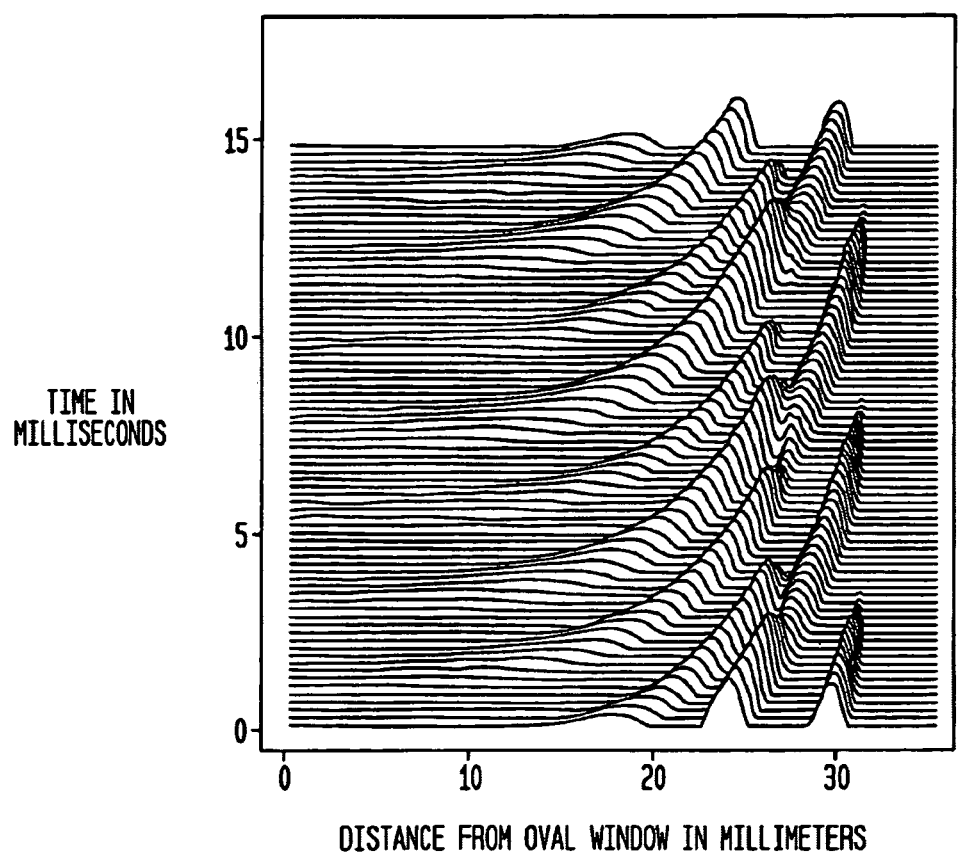
FIG. 3 is a graph illustrating a travelling wave excitation pattern for tones at 470 and 200 Hz.

When the stimulation is viewed as a 3D pattern, several consequences become more apparent a) A whole pattern is easier to recognize than a partial pattern because it contains more information. This characteristic is also important for grouping sound components from the same source. Some of the temporal and spatial coherence of excitation patterns arising from a single sound source is lost when the signal is bandpass filtered into separate components that are encoded independently of one another. Conversely, sounds from different sources will be easier to separate if each one gives rise to a whole pattern, rather than a number of independent components which must be recombined by the perceptual mechanism into an unknown number of sound sources. In the particular case of speech in background noise, it is important that the speech and the noise both produce complete 3D excitation patterns so that the perceptual mechanisms can use this information to allocate components of the combined pattern more easily to the noise or to the speech.

b) Dynamic patterns are easier to recognise than stationary ones. If is well-known that the tactile system provides increased information about texture, shape and edges of objects if the fingers are moved over the surface of the object than if a static contact is made. In a similar way, the spacing of ridges in the 3D auditory excitation pattern may be enhanced perceptually by sweeping them along the cochlea. Similarly, onsets and offsets of sounds correspond to edges in the 3D pattern, and these may be perceived more clearly as they move along the cochlea, rather than just appearing with different amplitudes at different parts of the cochlea and then disappearing again. Thus the presentation of dynamic patterns may improve frequency discrimination and resolution and perception of onsets and offsets of sounds with complex spectra.

c) If a pattern is known to vary smoothly and regularly, missing sections can be interpolated or filled in. For example, one can "see" what is on the other side of a paling fence as one walks past even though most of the scene is obscured by the fence at any one time. This is because the visual system is able to reconstruct the continuous picture from the parts that are viewed at separate instants in time. In the case of auditory signals that are obscured by noise, parts of a smoothly varying, regular speech pattern may be perceived through temporal and spectral gaps in the noise and reconstructed in an analogous manner. However, if the speech and noise patterns do not vary smoothly with position, this reconstruction is much more different this is a potential explanation for the fact that implant users are unable to recognize speech in noise when the signal-to-noise ratio is close to zero. The travelling wave processor may allow listeners to reconstruct lower amplitude speech signals even when they are partially obscured by more intense noise signals, provided that there are some temporal or spectral gaps in the noise signal.

d) Tone complexes with harmonically related components produce 3D patterns with special characteristics in the regions where the tonal patterns overlap. These characteristics are not present in anharmonic complexes. They are also not present in the excitation patterns produced by existing cochlear implant sound processors because they do not produce overlapping patterns for individual tones separated by an octave or more. For example, FIG. 2 shows the excitation pattern for 2 tones at 200 and 600 Hz. In the overlap region, every third diagonal ridge is larger than the others because of the constructive addition of the two excitation patterns. FIG. 3 shows an anharmonic combination where there is no regular summation of the two patterns in the overlap region.

The travelling wave in normal hearing has been recognised and discussed in the scientific literature. However, this literature has had virtually no effect on the design of cochlear implants or hearing aids as far as the inventors are aware. One explanation for this is that the frequency response of the cochlea to sinusoidal signals is highly peaked and implant and hearing aid designers have chosen to ignore the low-frequency tails of the frequency response curves. The closest existing technologies are cochlear implant sound coding schemes that measure spectral characteristics of input signals with bandpass filters and represent them by stimulating individual electrodes.

The preferred implementation of the present invention utilizes a digital-signal-processor to calculate an approximate travelling wave excitation pattern from a digitised input signal. The travelling wave pattern is essentially a specification of the displacement of each point on the basilar membrane of the cochlea as a function of time and position. The implementation is based directly on published experimental data from normally-hearing human subjects rather than theoretical models of basilar membrane mechanics. The implementation is also simplified to make it feasible for real-time implementation and to make it easier to parameterize the fitting procedure for individual cochlear implant users.

Figure 4:
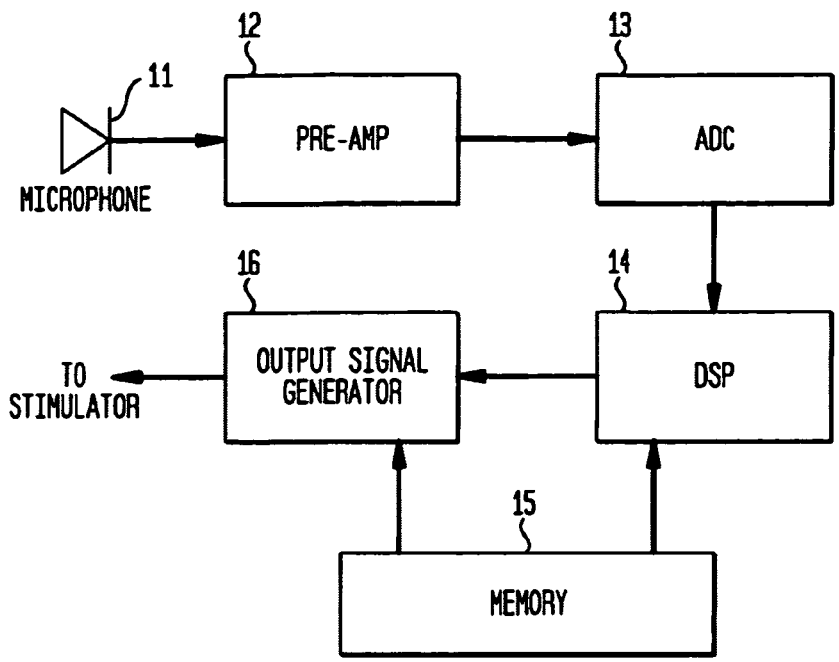
FIG. 4 is a schematic illustration of one implementation of the invention.

One embodiment of the system according to the present invention is shown in FIG. 4, with the components of the system as listed below.

Figure 5:
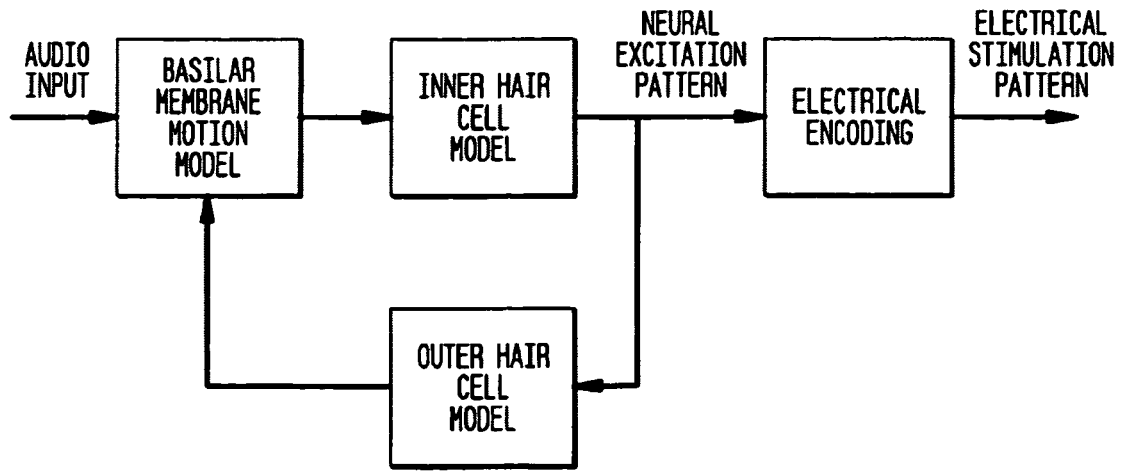
FIG. 5 is a block diagram of one speech processing implementation of the present invention.

1. Microphone 11 to convert an acoustic input signal to an electrical signal
2. Preamplifier/Automatic Gain Control 12 to amplify and control the level of the electrical signal.
3. Analog-to-Digit-Converter 13 to convert the electrical signal to a stream of digital samples.
4. Digital-Signal-Processor 14 to calculate the travelling wave pattern and convert it to an electrical stimulus pattern.
5. Programmable Memory 15 to store patient-specific parameters, the processor programs, and intermediate results in calculating the traveling wave pattern.
6. Output Signal Generator 16 to control a cochlear implant and deliver the electrical stimulus to the implant patient A simpler version of the present invention, in particular the digital signal processor, is shown in FIG. 5. In this particular aspect the invention essentially resides in a system consisting of four main parts, a Basilar Membrane Motion Model which accepts an audio signal as input and calculates the displacement or velocity of the basilar membrane at each electrode position; an Inner Hair Cell Model which calculates the amount of neural excitation at each electrode position based on the information received from the Basilar Membrane Motion Model; an Outer Hair Cell Model which provides a feedback path that takes into consideration the amount of neural excitation calculated by the Inner Hair Cell Model and the affects such excitation will have on the Basilar Membrane Motion Model; whereby the amount of neural excitation affects the response of the Basilar Membrane Motion Model; and an Electrical Encoding Component which calculates the pattern of electrical stimulation which will provide the desired neural excitation pattern. Each of these 4 components will be described in more detail below.

Basilar Membrane Motion Model

The Basilar Membrane Motion Model accepts an audio signal as input and is calculates the displacement or velocity of the basilar membrane at each electrode position in relation to the audio signal.

One possible embodiment of the Basilar Membrane Motion Model consists of the following steps, which are repeated continuously:

1 The input audio signal is divided into short overlapping frames. Each frame contains L consecutive samples of the audio signal, and is defined as the column vector X1. A suitable length is L=128. Each frame heavily overlaps with the previous frame, and contains K new data points. A suitable value is K=1.

2 Multiply the input frame vector X1 point-by-point by a window vector W, resulting in a column vector X2 of length L, according to:

$$X2(n)=X1(n)*W(n)$$

for n=0 to L−1.

A suitable window function is the Hann function, defined as:

$$W(n)=0.5*(1-\cos(2*n*pi/L)$$

for n=0 to L−1.

3 Calculate the L-point Fast Fourier Transform (FFT) of Me column vector X2. This results in a column vector X3 of length L, with complex values. Because X2 is real, X3 has Hermitian symmetry, and the last L/2 samples can be discarded (or not calculated). From the first L/2 samples, only the real parts are required and the imaginary parts are discarded (or not calculated). The output is a real column vector X4 of length L/2.

4 Multiply column vector X/4 by a rectangular weights matrix G, according to:

$$X5=G*X4.$$

The weights matrix G has N rows and L/2 columns. The output is a column vector X5 of length N, where N is the number of channels. The weights matrix G determines the frequency magnitude response of each channel, and is further described below.

5 Delay each channel by a time delay specified by column vector D, which has length N, according to the formula:

$$X6(k,t)=X5(k,t-D(k))$$

for k=1 to N

Figure 7:
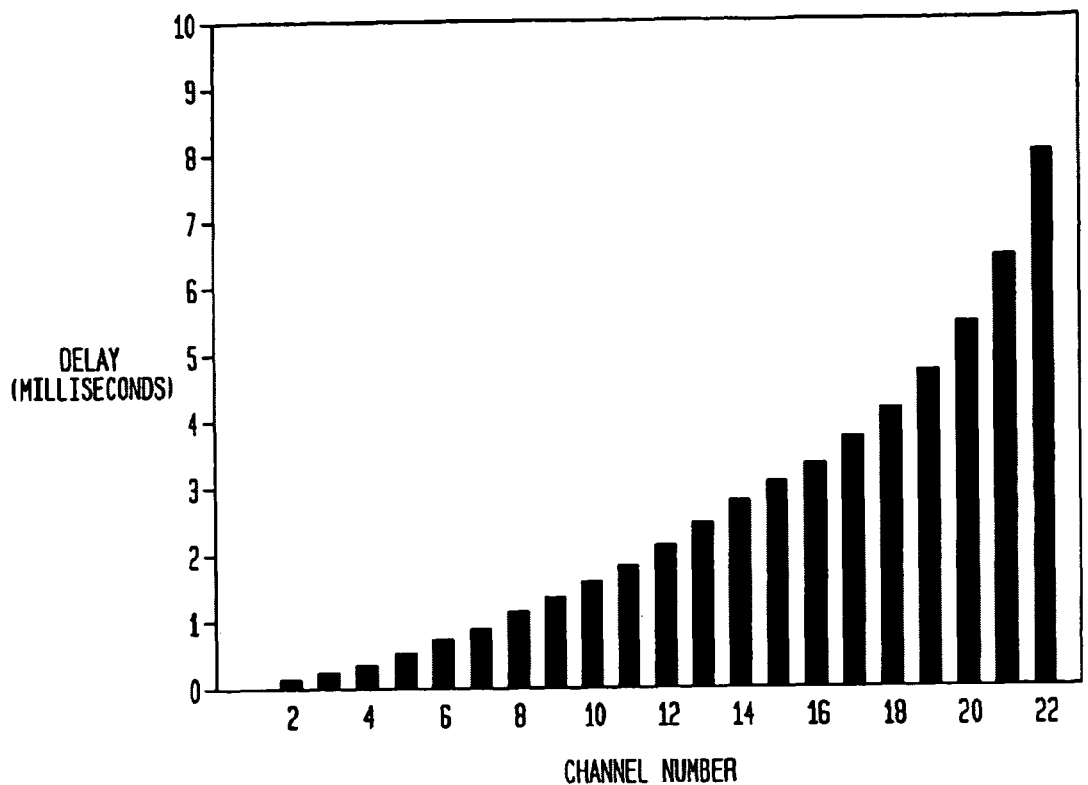
FIG. 7 is a graph depending the typical delay of each of each of the 22 channels.

Typical delays for a 22-channel processor are shown in FIG. 7. The delay varies from zero delay at channel 1 (the most basal channel to 8 milliseconds at channel 22 (the most apical channel).

The output is a column vector X6 of length N, where each element is a sample of one channel of the Basilar Membrane Motion Model.

Each row of the matrix W represents the amplitude and phase of the FFT frequency components at the position of one of the electrodes in the cochlea relative to the amplitude and phase at the stapes (the input to the cochlea). The phase difference is equal to 2 pi times the time taken for the travelling wave to travel from the stapes to the position of the electrode multiplied by the frequency of the FFT component. The amplitude difference between the stapes and the electrode position is proportional to the response of the basilar membrane at the position of the electrode to a pure tone at the frequency of the FFT component (or alternatively, the tuning curve of a neuron at the position of the electrode). The amplitude coefficients at each electrode position have a peaked shape with the maximum at the FFT frequency closest to the characteristic frequency at the individual electrode position, and the amplitudes of FFT coefficients higher than this frequency fall rapidly to zero.

An alternative way of implementing the delays in this system is by shifting the FFT window back in time by a different amount for each electrode. If the shift is chosen to be equal to the time taken for the travelling wave to travel from the stapes to the electrode position, then the coefficients of the matrix W are all real (ie the phase is zero for all FFT components).

The weights matrix G can be calculated according to the following steps:

The characteristic frequency of each channel is determined based on the position of the electrodes in the cochlea, according to Greenwood's formula. A further correction to the characteristic frequency of each channel should be applied to account for the fact that electrodes at a particular position in the cochlea actually stimulate neurons with a lower characteristic frequency than that predicted by Greenwood's formula (Blarney P J, Dooley G J, Parisi E S and Clark G M., Pitch comparisons of acoustically and electrically evoked auditory sensations. Hearing Research, 99, 139-150, 1996; James C, Blarney P J, Shallop J K, Incerti P V & Nicholas A M. Contralateral masking in cochlear implant users with residual hearing in the non-implanted ear, audiology and Neuro-Otology, 6, 87-97, 2001). This correction factor implies that the effective distance of the electrode from the stapes is greater by a factor of 2.625/1.875. Alternatively, for subjects who have previously used another sound processor and have become accustomed to a particular frequency-to-electrode map, those frequencies can be used. The characteristic frequencies are stored in a vector C of length N.

2. The centre frequency of each FFT bin is calculated and stored in vector B, of length L/2.

Figure 6:
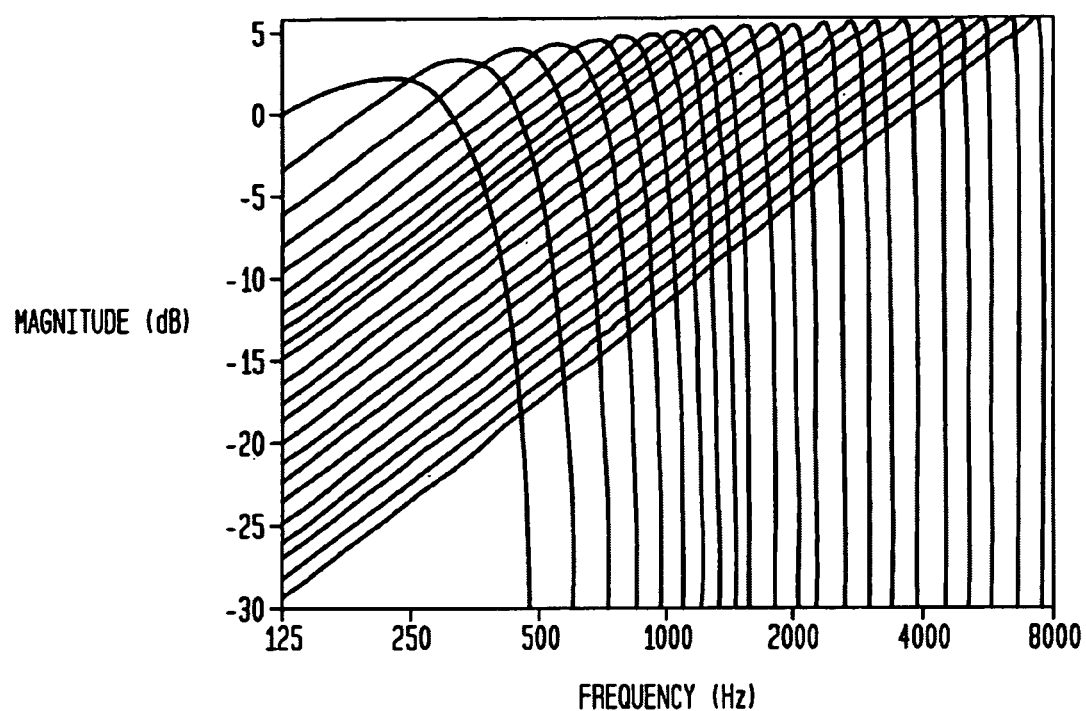
FIG. 6 is a graph of the typical frequency response of a 22-channel filterbank.

3. The weights matrix element G(k, b) represents the gain of channel k at the centre frequency of FFT bin b, and can be calculated according to the formula:

$B(b) <= C(k)$ $G(k,b) = \{B(b)/C(k)\}^E$ else $G(k,b) = 0$ where the symbol "^" means "to the power of" and the parameter E is called the gain exponent. Suitable values for E are in the range 1 to 5. Suitable choices for characteristic frequencies for 22 channels, with a gain exponent E=1 result in the magnitude response shown in FIG. 6.

The amplitude of each FFT component at each electrode position is represented by the magnitude of the corresponding element in matrix W. These amplitudes may be estimated from psychophysical tuning curves in humans with normal hearing (Zwicker, E. On a psychophysical equivalent of tuning curves. In Zwicker E. & Terhardt E (eds) Facts and models in healing. pp 132-141, Berlin: Springer-Verlag, 1974), from estimates of excitation in the loudness models of Zwicker (Zwicker E. Masking and psychological excitation as consequences of the ear's frequency analysis, in Plomp R & Smoorenburg G F (Eds) Frequency analysis and periodicity detection in hearing, pp 376-96, Leiden: A W Sijthoff, 1970.) or Moore & Glasberg (Moore B C J & Glasberg B R. A model of loudness perception applied to cochlear hearing loss. Auditory Neuroscience 3, 289-311, 1997) or from an approximation or from an empirical function designed to optimise the travelling wave processor for individual implant users.

Inner Hair Cell Model

The Inner Hair Cell Model calculates the amount of neural excitation at each electrode position based on the displacement or velocity of the basilar membrane at each electrode position in relation to the audio signal as calculated by the Basilar Membrane Motion Model as discussed above. A simple embodiment of the Inner Hair Cell Model is a half-wave rectifier, with other embodiments possible as would be obvious to those skilled in the art. The half wave rectification mimics the response of the hair cells in a normal cochlea. The amplitude of the half-wave rectified travelling wave at each electrode position is represented by the current level (or electric charge, or pulse width) of an electric pulse on that electrode. This mapping from amplitude to electrical stimulation parameters differs from conventional cochlear implant mapping in that the instantaneous amplitude of the travelling wave is represented rather than a smoothed amplitude or intensity which is averaged over a time window of several milliseconds. Conventional processors code the amplitude envelope rather than the instantaneous amplitude, and in doing so, they lose much of the temporal information carried by the signal itself. The coding of instantaneous amplitude is especially important to the travelling wave processor because coding envelope information would merely smear out the information from different frequency components rather than providing the detailed timing information illustrated in FIGS. 1-3. In particular the 3-dimensional ridges would become much broader in both spatial and temporal dimensions, and would lose their characteristics.

Outer Hair Cell Model

The Outer Hair Cell model aims to emulate the non-linearity that is observed in the response of a person with normal hearing. This is performed by providing a feedback path to the Basilar Membrane Motion Model which takes into consideration the proposed neural excitation pattern and the affects such a pattern has on the response of the Basilar Membrane Motion Model. The output of the Inner Hair Cell Model is an estimate of the neural excitation pattern that would be present in a person with normal hearing. It has been found that the gain for low-amplitude audio signals is greater than the gain for large-amplitude audio signals. This component is optional and may be omitted in a simplified implementation.

Electrical Encoding Component

The Electrical Encoding component calculates the pattern of electrical stimulation that will provide the desired neural excitation pattern. There are several possible embodiments of the Electrical Encoding component and some components that are used in the prior art of cochlear implant processors can be used to perform this function according to the present invention. It is important to note that it is the instantaneous amplitude of the waveform at each electrode position which is coded as the current level (or electric charge or pulse width) of an electric pulse on that electrode. This differs greatly from prior art systems where it is the time-averaged amplitude envelope of the waveform which constitutes what is coded as the current level of an electric pulse on that electrode. In essence, the conversion is effected by means of a function relating the amplitude to electric current level derived from prior measurements for each electro which may be stored in the memory 15.

The present invention can be used with implants that allow both simultaneous and/or non-simultaneous stimulation. If the invention is used on an implant that stimulates channels simultaneously, the traveling wave amplitudes at individual electrode positions can be represented by simultaneous electric currents (analog rather than pulsatile stimuli) on each individual electrode.

Figure 8:
FIG. 8 is a block diagram showing the sub-components of the Electrical Encoding Component of FIG. 5.

If the invention is used with an implant that stimulates channels sequentially (nor-simultaneously), then the Electrical Encoding component can be divided into two sub-components as illustrated in FIG. 8. The Sampler component samples the neural excitation pattern such that each output sample produces one electrical pulse. The Amplitude Mapping component calculates the electrical parameters of the pulse, such as current level and pulse width.

One simple embodiment of the Sampler component is taken from the well-known Continuous Interleaved Sampling (CIS) processor. The neural excitation pattern is sampled in a round-robin fashion at a uniform rate on each channel, so the sampling rate is equal to the simulation rate on each channel. The samples are interleaved across channels so that the electrical pulses are sequential (non-overlapping). The rate must be sufficiently high so that the time waveform of the neural excitation on each channel is adequately represented. Typically this requires more than 1000 pulses per second on each channel.

Note that in a standard CIS processor the filters are designed to be non-overlapping and relatively narrow, and the smoothed envelope of the filter outputs are sampled. In contrast, the present invention has broad, heavily overlapping filters and the instantaneous amplitude of the half-wave rectified filter output is sampled.

The CIS Sampler embodiment has the disadvantage that high stimulation rates are required. An alternative embodiment, which is new in this invention, is called the Time Interval Maxima Sampler. It reduces the total simulation rate that is required. It has the following steps:

1. The neural excitation pattern is divided into short non-overlapping time intervals. Each time interval can be represented as a matrix X that has N columns, where N is the number of channels, and T rows, where T is the number of time samples of the neural excitation pattern in each time interval. The duration of the time interval is equal to the time taken to output a number M of electrical pulses, where M is less N.

2. In each time interval the maximum value of each channel is calculated, i.e. the maximum of the matrix X across the rows. The output is a column vector Y with N columns, one for each channel.

3. The amplitudes of the N samples in column vector Y are examined, and the M largest samples are retained. Each of these M samples produces one electrical pulse. The pulses are output in the next time interval.

The Amplitude Mapping component can be the same as that used in the prior art Continuous Interleaved Sampling (CIS) processor or Spectra Maxima Sound Processor (SMSP). It has the following steps:

1. The amplitude of each sample is compressed by a non-linear function known as a loudness growth function, which typically has a logarithmic shape. Each output P represents a proportion of the electrical dynamic range.

2. The current level L of each electrical pulse is calculated from the output P and the previously measured threshold T and maximum comfortable level C (for that channel) as:

$$L=T+(C-T)*P$$

Following this, the electrode(s) to be stimulated are selected, and the output signal generator 16 is fed the data required to produce the electrical stimulus pulses.

It will be appreciated that there are various ways of implementing the present invention, for example using circuitry to provide the travelling wave type stimuli, which are included within the scope of the present inventive concept. Variations and additions are also possible within the general inventive concept disclosed.

The invention claimed is:

1. A sound processor for generating electrical stimuli in an auditory prosthesis having an electrode array implanted in a cochlea, the sound processor comprising:
    a microphone;
    an analog-to-digital converter electronically coupled to the microphone to receive electronic signals from the microphone, wherein the electronic signals are generated in response to a sound signal, and the analog-to-digital converter is adapted to convert the electronic signals into digital samples;
    a processor electronically coupled to the analog-to-digital converter to receive the digital samples, the processor being adapted to calculate a traveling wave pattern from the digital samples and generate a stimulus pattern from the calculated traveling wave pattern; and
    an output signal generator in electronic communication with the processor, the output signal generator being adapted to generate a neural excitation signal from the stimulus pattern and output the neural excitation signal to the electrode array such that the electrode array presents the neural excitation signal and stimulates a neural excitation pattern in the cochlea which approximates a spatio-temporal pattern associated with a traveling wave generated on the basilar membrane in a normally-hearing cochlea when stimulated by the sound signal.

2. The sound processor of claim 1, wherein the processor calculates the traveling wave pattern by processing the digital samples according to a predetermined instruction set.

3. The sound processor of claim 2, wherein the predetermined instruction set includes a data feedback loop.

4. The sound processor of claim 3, wherein the data feedback loop generates an estimate of an amount of neural excitation resulting from the stimulus pattern and incorporates the estimate into the predetermined instruction set.

5. The sound processor of claim 1, wherein the processor calculates a neural excitation level at each electrode position in a normally-hearing cochlea when stimulated by the sound signal.

6. The sound processor of claim 5, further including:
    a half-wave rectifier, wherein the neural excitation level is calculated using the half-wave rectifier.

7. The sound processor of claim 1, wherein the processor is adapted to generate the stimulus pattern based upon an instantaneous amplitude of the calculated traveling wave pattern at each respective electrode position.

8. The sound processor of claim 7, wherein the instantaneous amplitude is a local maximum amplitude of the calculated traveling wave pattern at each respective electrode position.

9. The sound processor of claim 1 further comprising a programmable memory electronically coupled to the processor.

10. The sound processor of claim 1 further comprising a signal amplifier electronically coupled between the microphone and the analog-to-digital converter.

11. The sound processor of claim 1, wherein the processor:
samples the digital samples to produce a data sample;
derives a vector of complex Fourier transform coefficients for the data sample;
multiplies the vector of the coefficients by a complex matrix representing a first amplitude and a first phase of Fourier frequency components according to electrode positions within the cochlea relative to a second amplitude and a second phase at a stapes in a normally-hearing cochlea to produce an output vector; and
converts values of the output vector into the stimulus pattern.

12. The sound processor of claim 1, wherein the processor determines a displacement of the basilar membrane at each electrode position in a normally-hearing cochlea when stimulated by the sound signal.

13. The sound processor of claim 1, wherein the processor determines a velocity of the basilar membrane at each electrode position in a normally-hearing cochlea when stimulated by the sound signal.

14. A cochlear implant, comprising:
the sound processor of claim 1,
wherein the cochlear implant includes the electrode array, wherein the electrode array is adapted to be implanted in a cochlea adjacent a basilar membrane of the cochlea and outputs an electrical signal to the cochlea, the electrical signal corresponding to the neural excitation signal.

15. A sound processor for generating electrical stimuli in an auditory prosthesis having an electrode array implanted in a cochlea adjacent a basilar membrane, the sound processor comprising:
a microphone adapted to generate electronic signals in response to a sound signal;
means for converting the electronic signals into digital samples;
means for processing the digital samples, including calculating a traveling wave pattern from the digital samples and generating a stimulus pattern from the calculated traveling wave pattern; and
means for generating a neural excitation signal from the stimulus pattern and output the neural excitation signal to the electrode array such that the electrode array presents the neural excitation signal and stimulates a neural excitation pattern in the cochlea which approximates a spatio-temporal pattern associated with a traveling wave generated on the basilar membrane in a normally-hearing cochlea when stimulated by the sound signal.

16. The sound processor of claim 15, wherein the means for processing the digital samples includes calculating the traveling wave pattern by processing the digital samples according to a predetermined instruction set.

17. The sound processor of claim 16, wherein the predetermined instruction set includes a data feedback loop.

18. The sound processor of claim 17, wherein the data feedback loop generates an estimate of an amount of neural excitation resulting from the stimulus pattern and incorporates the estimate into the predetermined instruction set.

19. The sound processor of claim 15, wherein the means for processing the digital samples includes calculating a neural excitation level at each electrode position in a normally-hearing cochlea when stimulated by the sound signal.

20. The sound processor of claim 19, further including:
a half-wave rectifier, wherein the neural excitation level is calculated using the half-wave rectifier.

21. The sound processor of claim 15 further comprising:
means for amplifying the electronic signals.

22. The sound processor of claim 15, wherein the means for processing the digital samples bases the stimulus pattern upon an instantaneous amplitude of the calculated traveling wave pattern at each respective electrode position.

23. The sound processor of claim 15, wherein the means for processing the digital samples includes:
sampling the digital samples to produce a data sample;
deriving a vector of complex Fourier transform coefficients for the data sample;
multiplying the vector of the coefficients by a complex matrix representing a first amplitude and a first phase of Fourier frequency components according to electrode positions within the cochlea relative to a second amplitude and a second phase at a stapes in a normally-hearing cochlea to produce an output vector; and
converting values of the output vector into the stimulus pattern.

24. The sound processor of claim 15, wherein the means for processing the digital samples includes determining a displacement of the basilar membrane at each electrode position in a normally-hearing cochlea when stimulated by the sound signal.

25. The sound processor of claim 15, wherein the means for processing the digital samples includes determining a velocity of the basilar membrane at each electrode position in a normally-hearing cochlea when stimulated by the sound signal.

26. The sound processor of claim 15, wherein the processor is adapted to generate the stimulus pattern based upon an instantaneous amplitude of the calculated traveling wave pattern at each respective electrode position.

27. A cochlear implant, comprising:
the sound processor of claim 15,
wherein the cochlear implant includes the electrode array, wherein the electrode array is adapted to be implanted in a cochlea adjacent a basilar membrane of the cochlea and outputs an electrical signal to the cochlea, the electrical signal corresponding to the neural excitation signal.

28. A sound processor for generating electrical stimuli in an auditory prosthesis having an electrode array implanted in a cochlea adjacent a basilar membrane, the sound processor comprising:
a microphone adapted to generate electronic signals in response to a sound signal;
a signal amplifier electronically coupled to the microphone;
an analog-to-digital converter electronically coupled to the signal amplifier to receive the electronic signals from the microphone, wherein the analog-to-digital converter is adapted to convert the electronic signals into digital samples;
a processor electronically coupled to the analog-to-digital converter to receive the digital samples, wherein the processor calculates a traveling wave pattern from the digital samples and generates a stimulus pattern from the calculated traveling wave pattern according to a predetermined instruction set by:
determining a displacement of the basilar membrane and calculating a neural excitation level at each electrode position in a normally-hearing cochlea when stimulated by the sound signal, and employing a data feedback loop based on the stimulus pattern, a programmable memory electronically coupled to the processor; and an output signal generator in electronic communication with the processor and the electrode array, the output signal generator being adapted to generate a neural excitation signal from the stimulus pattern and output the neural excitation signal to the electrode array such that the electrode array presents the neural excitation signal and stimulates a neural excitation pattern in the cochlea which approximates a spatio-temporal pattern associated with a traveling wave generated on the basilar membrane in a normally-hearing cochlea when stimulated by the sound signal.

29. The sound processor of claim 28, wherein the processor is adapted to generate the stimulus pattern based upon an instantaneous amplitude of the calculated traveling wave pattern at each respective electrode position.

30. The sound processor of claim 29, wherein the instantaneous amplitude is a local maximum amplitude of the calculated traveling wave pattern at each respective electrode position.

31. The sound processor of claim 28, wherein as part of the predetermined instruction set, the processor:

samples the digital samples to produce a data sample;

derives a vector of complex Fourier transform coefficients for the data sample;

multiplies the vector of the coefficients by a complex matrix representing a first amplitude and a first phase of Fourier frequency components according to electrode positions within the cochlea relative to a second amplitude and a second phase at a stapes in a normally-hearing cochlea to produce an output vector; and converts values of the output vector into the stimulus pattern.

32. The sound processor of claim 28, further including:

a half-wave rectifier, wherein the neural excitation level is calculated using the half-wave rectifier.

33. The sound processor of claim 28, wherein the data feedback loop generates an estimate of an amount of neural excitation resulting from the stimulus pattern and incorporates the estimate into the predetermined instruction set.

34. A cochlear implant, comprising:

the sound processor of claim 28, wherein the cochlear implant includes the electrode array, wherein the electrode array is adapted to be implanted in a cochlea adjacent a basilar membrane of the cochlea and outputs an electrical signal to the cochlea, the electrical signal corresponding to the neural excitation signal.

* * * * *